(12) United States Patent
New, Jr. et al.

(10) Patent No.: US 6,494,829 B1
(45) Date of Patent: Dec. 17, 2002

(54) PHYSIOLOGICAL SENSOR ARRAY

(75) Inventors: William New, Jr., Woodside, CA (US); Andrea J. Harry, Cambridge (GB); Paul Johnson, Oxford (GB); Harpal S. Kumar, Cambridge (GB); William J. Mullarkey, Wigan (GB); Laurence J. Nicolson, Liverpool (GB); John D. Place, Suffolk (GB)

(73) Assignee: Nexan Limited, Cambridge (GB)

( * ) Notice: Subject to any disclaimer, the term of this patent is extended or adjusted under 35 U.S.C. 154(b) by 0 days.

(21) Appl. No.: 09/292,159

(22) Filed: Apr. 15, 1999

(51) Int. Cl.$^7$ ................................................. A61B 5/00
(52) U.S. Cl. ........................ 600/300; 128/903; 600/508
(58) Field of Search ................................ 600/300–301, 600/481–486, 500, 529–538, 508, 544–545; 128/903–904, 920–925

(56) References Cited

U.S. PATENT DOCUMENTS

| | | | |
|---|---|---|---|
| 2,298,125 | A | 10/1942 | Hartman |
| 2,660,165 | A | 11/1953 | Miller |
| 3,212,496 | A | 10/1965 | Preston |
| 3,409,007 | A | 11/1968 | Fuller |
| 3,572,316 | A | 3/1971 | Vogelman et al. |
| 3,572,322 | A | 3/1971 | Wade |
| 3,603,881 | A | 9/1971 | Thornton |
| 3,757,778 | A | 9/1973 | Graham |
| 3,848,582 | A | 11/1974 | Milani et al. |
| 3,858,576 | A | 1/1975 | Dehnert et al. |
| 3,882,277 | A | 5/1975 | DePedro et al. |
| 3,902,478 | A | 9/1975 | Konopasek et al. |
| 3,908,641 | A | 9/1975 | Judson et al. |

(List continued on next page.)

FOREIGN PATENT DOCUMENTS

| | | |
|---|---|---|
| CH | 293560 | 12/1953 |
| EP | 0 212 278 | 3/1987 |

(List continued on next page.)

OTHER PUBLICATIONS

"Microcomputer–based Telemetry System for ECG Monitoring," *Proceedings of the Ninth Annual Conference of the IEEE Engineering in Medicine and Biology Society*, The Boston Park Plaza Hotel, Boston, MA, Nov. 13–16, 1987, vol. 3 of 4, 2 pages.

"Biomedical Telectrodes: Compact transmitters would eliminate the need for wires to monitors," *NASA TechBrief*, Lyndon B. Johnson Space Center, Houston, Texas, Feb., 1990, 1 page.

*Primary Examiner*—Robert L. Nasser
*Assistant Examiner*—Michael Astorino
(74) *Attorney, Agent, or Firm*—Woodcock Washburn Kurtz Mackiewicz & Norris LLP

(57) ABSTRACT

A physiological sensor device for attachment to a mammalian subject comprising an output transmitter, at least two physiological sensors each for sensing one of the subject's physiological parameters, and a controller operably in communication with the physiological sensors which controller communicates a signal comprising data representative of both the sensed physiological parameters to the output transmitter which operably transmits the signal to a remote location, wherein the controller comprises a multiplexer which operably switches the data from both the physiological sensors into a serial output signal. Respiration may be detected by a bend sensor including an elongate member and an electrical component mounted thereon which electrical component has an electrical property which varies in dependence on the extent of bending of the elongate member. Other parameters such as temperature and full waveform ECG may also be measured.

21 Claims, 6 Drawing Sheets

U.S. PATENT DOCUMENTS

| | | | |
|---|---|---|---|
| 3,943,918 A | 3/1976 | Lewis | |
| 3,986,498 A | 10/1976 | Lewis | |
| 4,023,564 A | 5/1977 | Valiquette et al. | |
| 4,082,087 A | 4/1978 | Howson | |
| 4,121,573 A | 10/1978 | Crovella et al. | |
| 4,121,575 A | 10/1978 | Mills et al. | |
| 4,122,843 A | 10/1978 | Zdrojkowski | |
| 4,141,351 A | 2/1979 | James et al. | |
| 4,202,344 A | 5/1980 | Mills et al. | |
| 4,233,987 A | 11/1980 | Feingold | |
| 4,249,538 A | 2/1981 | Musha et al. | |
| 4,319,241 A | 3/1982 | Mount | |
| 4,328,814 A | 5/1982 | Arkans | |
| 4,353,372 A | 10/1982 | Ayer | |
| 4,356,486 A | 10/1982 | Mount | |
| 4,494,553 A | 1/1985 | Sciarra et al. | |
| 4,522,211 A | 6/1985 | Bare et al. | |
| 4,593,284 A | 6/1986 | Clifford et al. | |
| 4,606,352 A | 8/1986 | Geddes et al. | |
| 4,622,979 A | 11/1986 | Katchis et al. | |
| 4,658,831 A | 4/1987 | Reinhard et al. | |
| 4,662,378 A | 5/1987 | Thomis | |
| 4,709,704 A | 12/1987 | Lukasiewicz | |
| 4,742,831 A | 5/1988 | Silvian | |
| 4,763,660 A | 8/1988 | Kroll et al. | |
| 4,784,162 A | 11/1988 | Ricks et al. | |
| 4,827,943 A | 5/1989 | Bornn et al. | |
| 4,852,572 A | 8/1989 | Nakahashi et al. | |
| 4,893,632 A | 1/1990 | Armington | |
| 4,909,260 A | 3/1990 | Salem et al. | |
| 4,926,868 A | 5/1990 | Larsen | |
| 4,955,381 A | 9/1990 | Way et al. | |
| 4,957,109 A | 9/1990 | Groeger et al. | |
| 4,967,748 A | 11/1990 | Cohen | |
| 4,967,749 A | 11/1990 | Cohen | |
| 4,981,141 A | 1/1991 | Segalowitz | |
| 4,984,572 A | 1/1991 | Cohen | |
| 4,986,270 A | 1/1991 | Cohen | |
| 5,027,816 A | 7/1991 | Cohen | |
| 5,038,782 A | 8/1991 | Gevins et al. | |
| 5,050,612 A | 9/1991 | Matsumura | |
| 5,069,215 A | 12/1991 | Jadvar et al. | |
| 5,078,134 A | 1/1992 | Heilman et al. | |
| 5,080,099 A | 1/1992 | Way et al. | |
| 5,163,429 A | 11/1992 | Cohen | |
| 5,168,874 A | 12/1992 | Segalowitz | |
| 5,199,433 A | 4/1993 | Metzger et al. | |
| 5,224,485 A | 7/1993 | Powers et al. | |
| 5,228,449 A | 7/1993 | Christ et al. | |
| 5,269,301 A | 12/1993 | Cohen | |
| 5,279,305 A | 1/1994 | Zimmerman et al. | |
| 5,307,817 A | 5/1994 | Guggenbuhl et al. | |
| 5,307,818 A | 5/1994 | Segalowitz | |
| 5,343,860 A | 9/1994 | Metzger et al. | |
| 5,353,793 A | 10/1994 | Bornn | |
| 5,372,125 A | 12/1994 | Lyons | |
| 5,373,852 A | 12/1994 | Harrison et al. | |
| 5,394,882 A | 3/1995 | Mawhinney | |
| 5,431,171 A | 7/1995 | Harrison et al. | |
| 5,456,682 A | 10/1995 | Edwards et al. | |
| 5,458,124 A | 10/1995 | Stanko et al. | |
| 5,462,051 A | 10/1995 | Oka et al. | |
| 5,465,715 A | 11/1995 | Lyons | |
| 5,511,553 A | 4/1996 | Segalowitz | |
| 5,522,396 A | 6/1996 | Langer et al. | |
| 5,538,005 A | 7/1996 | Harrison et al. | |
| 5,544,661 A | 8/1996 | Davis et al. | |
| 5,549,113 A | 8/1996 | Halleck et al. | |
| 5,558,638 A | 9/1996 | Evers et al. | |
| 5,564,429 A | * 10/1996 | Bornn et al. | 600/300 |
| 5,579,001 A | 11/1996 | Dempsey et al. | |
| 5,579,775 A | 12/1996 | Dempsey et al. | |
| 5,586,552 A | 12/1996 | Sakai | 128/633 |
| 5,617,871 A | 4/1997 | Burrows | |
| 5,634,468 A | 6/1997 | Platt et al. | |
| 5,652,570 A | 7/1997 | Lepkofker | |
| 5,670,944 A | 9/1997 | Myllymäki | |
| 5,678,545 A | 10/1997 | Stratbucker | |
| 5,682,902 A | 11/1997 | Herleikson | |
| 5,687,734 A | 11/1997 | Dempsey et al. | |
| 5,724,025 A | * 3/1998 | Tavori | 600/300 |
| 5,749,365 A | 5/1998 | Magill | 128/671 |
| 5,891,044 A | 4/1999 | Golosarsky et al. | |
| 6,015,387 A | * 1/2000 | Schwartz et al. | 600/504 |

FOREIGN PATENT DOCUMENTS

| | | |
|---|---|---|
| EP | 0 479 857 B1 | 12/1993 |
| EP | 0 617 914 A1 | 10/1994 |
| EP | 0 458 883 B1 | 11/1996 |
| EP | 0 760 224 A1 | 3/1997 |
| EP | 0 761 160 A1 | 3/1997 |
| EP | 0 770 349 A1 | 5/1997 |
| EP | 0 719 108 B1 | 6/1997 |
| EP | 0 796 589 A1 | 9/1997 |
| EP | 0 796 590 A1 | 9/1997 |
| EP | 0 598 016 B1 | 10/1997 |
| GB | 2 003 276 A | 3/1979 |
| GB | 2 207 579 A | 2/1989 |
| WO | WO 87/06447 | 11/1987 |
| WO | WO 90/01898 | 3/1990 |
| WO | WO 91/00054 | 1/1991 |
| WO | WO 93/02622 | 2/1993 |
| WO | WO 93/08734 | 5/1993 |
| WO | WO 93/10706 | 6/1993 |
| WO | WO 93/19667 | 10/1993 |
| WO | WO 94/01039 | 1/1994 |
| WO | WO 94/03105 | 2/1994 |
| WO | WO 94/25841 | 11/1994 |
| WO | WO 95/07048 | 3/1995 |
| WO | WO 95/07652 | 3/1995 |
| WO | WO 95/10974 | 4/1995 |
| WO | WO 96/01585 | 1/1996 |
| WO | WO 96/29005 | 9/1996 |
| WO | WO 96/38080 | 12/1996 |
| WO | WO 97/09923 | 3/1997 |
| WO | WO 97/28736 | 8/1997 |
| WO | WO 97/40747 | 11/1997 |

\* cited by examiner

PHYSIOLOGICAL SENSOR ARRAY

BACKGROUND OF THE INVENTION

1. Field of the Invention

The present invention relates to a physiological sensor device or sensor array for attachment to a mammalian subject in order to obtain data about one or more physiological parameters of the subject. In particular, the invention relates to a physiological in sensor device in the form of a patch attachable to the chest of a human subject to enable sensing of physiological data such as electro-cardiographic data and/or respiration data.

2. Description of the Prior Art

The prior art includes U.S. Pat. No. 3,943,918 to Lewis which discloses an ECG signal sensing and transmitting device for use in the care of medical patients requiring monitoring of cardiac functions. The device disclosed is a single use, disposable unit consisting principally of a foam pad having a pair of circular electrodes in one face of the rectangular foam block. The block comprises electrical circuitry which transmits an RF signal to a receiver which is required to be within 100 feet of the patient. Subsequent filtering and amplification of the signal takes place at a monitoring station comprising a receiver and the like. The device is disposable after one use but, as a result, is somewhat crude and only comprises two electrodes for very basic ECG measurements.

U.S. Pat. No. 4,121,573 discloses a chest sensor for monitoring cardiac rhythms of a patient using a pair of spaced circular electrodes mounted on a foam pad. Electrical connectors between the electrodes and electronic circuitry for acquiring and transmitting cardiac rhythm signals is provided by independent electrical leads or wires. The circuitry and wires are located on the rear surface of a first layer of foam and held in position by a second layer of foam. Accordingly, a fairly deep configuration of layers of foam, electronic circuitry and electrodes is provided in this rather crude two electrode device.

U.S. Pat. No. 4,957,109 discloses an electrode array for use in generating electrocardiographic signals for a patient. The array comprises ten different electrode regions (comprising pairs of semicircular electrodes) for attachment to different parts of the human body. The electrodes are interconnected to an output connector for attachment to signal processing apparatus. The electrode sensors and electrical conductors between the electrodes and the output conductor are formed on a large flexible circuit board having a large dentritic or tree-like configuration to enable location of the electrodes at appropriate positions on the human body for standard twelve lead diagnostic electrocardiogram studies. A digital infra red signal having multiplexed data from each of the ECG electrodes is transmitted to a remote location in use. While fairly sophisticated, this arrangement only contemplates point-in-time 12 lead ECG studies and is not disposable.

U.S. Pat. No. 5,634,468 discloses a sensor for physiological monitoring of a patient, consisting of a rectangular patch having a central structural member formed of MYLAR™ encased in an adhesive hydrogel. One side of the sensor has four circular electrodes for contacting the patient. The electrodes are wired to an electronic package on the opposite side of the structural member. The electronics package is adapted to receive ECG data and transmits the data to a monitoring unit. However, this small sensor is limited to measuring ECG signals.

U.S. Pat. No. 5,353,793 discloses sensor apparatus for making ECG measurements comprising a band which passes entirely round a patient's chest. The chest band can have optional shoulder straps and an optional abdominal band. Electrodes are positioned around the inner circumferential surface of the band for monitoring respiration, pulse and ECG signals. The ECG electrodes are simple conductive sensors in electrical contact with the skin. The pulse and respiration sensor comprises a tension sensor consisting of a piezoelectric element A minimum of 7 ECG sensors is provided but up to 18 can be spaced around the band. Two or more of the piezoelectric sensors can be provided in a single chest band. The various sensors are connected by cabling and accordingly the apparatus as a whole is quite bulky. Also, the data from the sensors is transferred to a remote location by wire via a connector. While the possibility of a radio link is mentioned, there is no detail as to how this would be achieved cost effectively to allow for disposability and yet ensure accurate and efficient data transfer from the various sensors.

International patent specification WO 94/01039 discloses physiological monitoring apparatus having a strip assembly for attachment to a patient's chest. The strip comprises a series of nine electrically conductive electrode sensors for attachment to the precordial region of a patient's chest for obtaining ECG data The strip only measures ECG data which is wirelessly transmitted on a multiplexed analog signal which modulates an RF carrier signal for transmission to a remote data analysis station which can be up to 50 to 100 meters from the strip. The emphasis here is to provide a complete ECG study of a patient using a portable system, and accordingly, there is no discussion of disposability and efficient communication of data from different types of sensors other than ECG.

SUMMARY OF THE INVENTION

An object of the invention is to avoid or at least mitigate the problems of the prior art. In particular, the invention seeks to provide an improved physiological sensor device which enables accurate and or continuous collection of various types of physiological data using a relatively inexpensive electrical system which can viably be disposed of after a single use over a 24 hour period. A further object of the invention is to provide a device which is able to collect a variety of types of physiological data, such as ECG, respiration, motion and/or temperature for example, while still being relatively inexpensive to manufacture. A yet further object is to use a single sensor for acquiring more than one type of physiological data.

Accordingly, a first aspect of the invention provides a portable and disposable physiological sensor device for attachment to a mammalian subject comprising physiological sensors for sensing the subject's physiological parameters, such as ECG or respiration, and a controller operably in communication with the physiological sensor for communicating a signal representative of the sensed physiological parameter to an output which operably transmits the signal to a remote location.

Preferably, at least two physiological sensors are provided, each for sensing different ones of the subject's physiological parameters. The controller is operably in communication with the physiological sensors so as to communicate a signal comprising data representative of both the sensed physiological parameters to an output transmitter which operably transmits the signal to a remote location. Preferably, the controller interleaves the data from both the physiological sensors into a serial output signal.

In a preferred embodiment, the controller of the invention comprises an application specific integrated circuit, and control circuits which are designed to have components communicate the signals between the sensor and output. Preferably, the output enables wireless transmission of the signal to a remote location, for example, using a digitally modulated electromagnetic carrier frequency such as a low frequency RF carrier for inductive coupling with a receiver. Also, the controller samples an analog signal from the physiological sensor and converts the sampled signal into a digital signal using an analog to digital converter.

Alternatively, a first and second respiration sensor may be provided, one of which preferably comprises a bend sensor locatable, for example, on the subject's chest and preferably over or adjacent the subject's pectoral muscle.

In accordance with the invention, the output preferably transmits a transmission signal comprising a data signal from two or more physiological sensors. Beneficially, the rate of transmission of the different signals from the two physiological sensors can be varied. Preferably, a first physiological sensor operably detects ECG data and the controller operably communicates a signal representative of the ECG data to the output transmitter at a first sampling frequency, and a second physiological sensor operably detects at least one of respiration, motion, and temperature data and operably communicates a signal representative of that data at a second sampling frequency to the output transmitter. Preferably, the first sampling frequency is as large as or greater than the second sampling frequency and, more preferably, approximately ten times greater than the second sampling frequency. For example, the first sampling frequency might be 250 Hz while the second sampling frequency might be 25 Hz.

According to another aspect of the invention, a disposable physiological sensor device for attachment to a mammalian subject is provided which is adapted for continuous use over a 24, or indeed longer, say 48, hour period, comprising a physiological sensor, a controller operably in communication with the physiological sensor which controller generates a signal representative of the subject's physiological parameters such as ECG or respiration, and an output for transmitting the signal to a remote location. Accordingly, the device is generally disposable after a single continuous use. Beneficially, two or more physiological sensors are provided on the device.

According to a further aspect of the invention, a physiological sensor device for attachment to a mammalian subject is provided comprising a bend sensor which comprises an elongate member and an electrical component mounted thereon which electrical component has an electrical property which varies in dependence on the extent of bending of the elongate member, and an electrical monitoring device for detecting variation in the electrical property of the electrical component thereby to determine a physiological parameter such as respiration, of a subject in use. Preferably, the electrical component comprises an elongate resistor superimposed on the elongate member. The resistor can comprise a track of conductive ink and a series of two or more areas of highly conductive material such as metallic material over the conductive ink, thereby to effect a series of individual conductive sensors having a combined resistance less than the track of conductive ink without the areas of highly conductive material. Preferably, the elongate resistor or track of conductive ink, is substantially U-shaped. The elongate member can comprise a flexible substrate such as MYLAR™. The device of the invention is preferably adapted to attach to a human chest for example over or adjacent the pectoral muscle of a subject and more preferably between a precordial position and the axilla of the subject in use, thereby to enable monitoring of the subject's respiration, for example.

A further aspect of the invention provides a physiological sensor device comprising two electrode sensors operably locatable on a patient, a current generator for driving a current to each of the electrode sensors, and an impedance measuring device for determining variation in the impedance of the electrode sensors when attached to the subject in use thereby to determine a variation in the motion of the subject in use due to variation in the impedance at the electrical sensors caused by such motion. Preferably, the current generator comprises a sine wave generator which operably independently drives each of the two electrode sensors. The impedance measuring device can comprise a differential amplifier having an input from each of the two electrode sensors. The output signal from the differential amplifier can pass through a filter and demodulator before being AC coupled to a further stage of amplification. Preferably, the current generator generates an alternating current and the impedance measuring device comprises an anti-aliasing device after the further stage of amplification to ensure proper detection of the impedance signal. Preferably, the two electrode sensors are drive electrodes in a four electrode sensor arrangement for monitoring subject respiration.

A yet further aspect of the invention provides a portable physiological sensor device comprising a plurality of electrode sensors for use in measuring electrocardiographic data and respiratory data of a subject, wherein at least one of the electrode sensors is used in both the electrocardiographic and respiratory measurements, and an output transmitter responsive to outputs of the electrodes sensors so as to enable wireless transmission of the electrocardiographic data and respiratory data to a remote location. Preferably, the signal from at least one electrode sensor is sampled periodically by an ECG measuring device at a first sampling frequency and periodically at a second sampling frequency by a respiration measuring device. Preferably, the first sampling frequency is greater than the second sampling frequency. In a preferred embodiment the first sampling frequency is approximately ten times greater than the second sampling frequency and, for example, can be 250 Hz compared to a second sampling frequency of 25 Hz.

A further aspect of the invention provides a physiological sensor device attachable to a mammalian subject in use and comprising two electrode sensors adapted to assist in monitoring one of electrocardiographic data, and respiratory data of the subject and further comprising a motion detector which operably monitors the variation in impedance between the two electrode sensors thereby to determine the extent of motion of the patient in use. Preferably, the device comprises a first respiration sensor having the two electrode sensors and two further electrode sensors, wherein one pair of the two electrode sensors and the two further electrode sensors forms a pair of drive electrodes to which drive current is operably applied, and the other pair of the two electrode sensors and the further electrode sensors forms a pair of input electrodes to the respiration sensor. Preferably, the first respiration sensor comprises a differential amplifier having an input from each of the input electrodes. Also, the device preferably comprises a second respiration sensor having, for example, a bend sensor. The device can further comprise a temperature sensor.

Another aspect of the invention provides a physiological sensor device for attachment to a mammalian subject comprising a sensor for acquiring physiological data about the subject in use, and an output transmitter which receives a signal representative of the physiological data from the sensor and transmits the signal to a remote location, wherein the output transmitter comprises an inductive element for inductively coupling the output transmitter to a remote receiver at the remote location. Beneficially the inductive coupling enables efficient low powered transfer of data from the device.

Preferably, the output transmitter comprises a reservoir capacitor and the inductive element, which together improve the power efficiency of transmission. Also, the inductive element preferably has first and second ends each of which ends is connected via one of a pair of switches to the supply lines within the output transmitter to enable a reversing of the polarity across the inductive element. Preferably, the inductive element comprises a coil which forms part of an and after "H-bridge" circuit in the output transmitter. In a preferred embodiment the inductive element comprises a rectangular, substantially flat coil.

A yet further aspect of the invention provides a physiological sensor device for attachment to a mammalian subject, having one or more physiological sensors, an output for transmitting a signal from the one or more physiological sensors to a remote location, and a memory for storing a serial number for identifying the physiological sensor device which serial number is transmittable by the output with the signal. The serial number may be randomly generated. The device may comprise a random number generator and a controller for selecting a randomly generated number from the random number generator and storing the selected randomly generated number as the device serial number in the memory.

Beneficially, each of the physiological sensors according to any aspect of the invention can comprise any one or more of the following: a first stage of amplification, possibly including a variable amplifier stage; a filter, for example, a band pass filter, and a demodulation stage to remove any carrier frequency. A further stage of amplification, again possibly including a variable amplifier stage, can be provided followed by an anti-aliasing stage and subsequent switched capacitor low pass filter stage before passing the signal through a controller including an ASIC and control circuits which drive signals from pre-selected sensors to an analog to digital converter which in turn can be fed to the output where the digital signal can be used to modulate a pre-selected carrier frequency.

BRIEF DESCRIPTION OF THE DRAWINGS

The invention will now be described, by way of example only, with reference to the accompanying drawings, in which.

DETAILED DESCRIPTION OF THE PRESENTLY PREFERRED EMBODIMENTS

Figure 1:
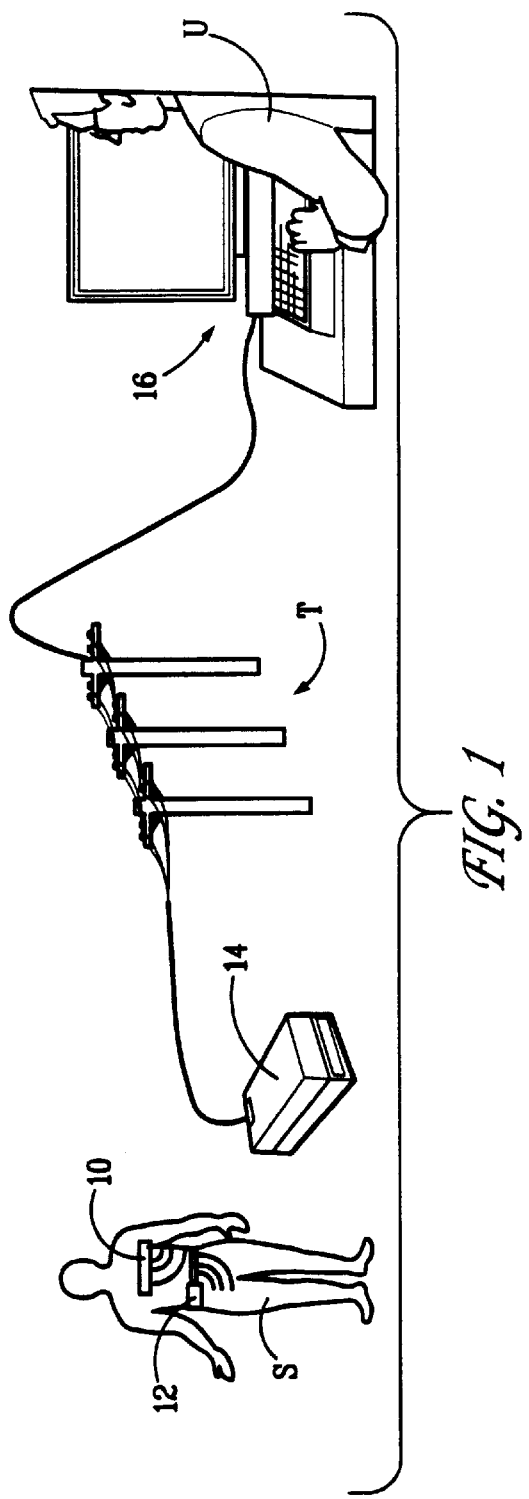
FIG. 1 is a schematic diagram of a physiological monitoring system in which a sensor device according to the invention can be suitably used.

FIG. 1 illustrates a physiological sensor device or array 10 according to the invention as attached to the chest of a human subject or patient S. Device 10 comprises an array of sensors 10a (to be described later), which generate data about the physiological condition of the subject. This data is transmitted to a portable signal transfer unit 12. In turn, signal transfer unit 12 transfers a signal representative of the measured physiological parameters to a base station 14 which operably communicates with a remote monitoring station 16, which can comprise a suitably programmed computer 16b. This communication is, for example, via a telemetry or telephonic link T, such as a land based telephone system, using, for example, modems 14c and 16a.

Figure 2:
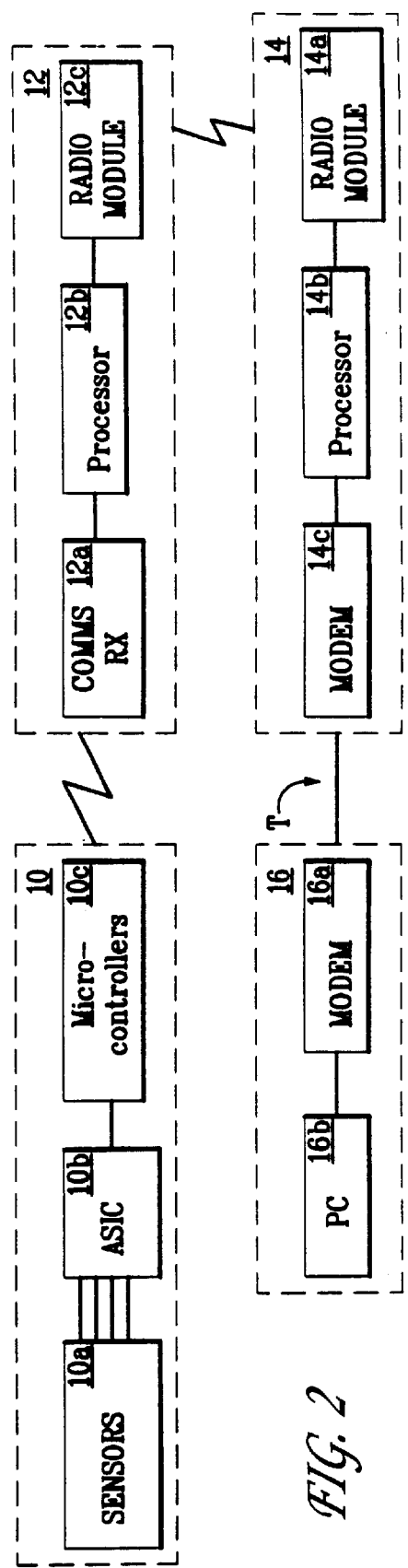
FIG. 2 is a schematic block diagram of the system shown in FIG. 1.

The basic structure of the different components in the system is shown in the schematic block diagram of FIG. 2. As can be seen, device 10 comprises an array of sensors 10a in communication with suitable electronics forming a controller for processing and communicating physiological data to the signal transfer unit 12. In this example, device 10 comprises an application specific integrated circuit (ASIC) 59, and at least one micro-controller 61. Further details of the preferred form of electronics and details of the sensors are described below, while further details of the structure and method of manufacture of the device 10 are given in our co-pending patent application entitled "Physiological Sensor Device", U.S. patent application Ser. No. 09/292,157, which is incorporated herein by reference.

The system further comprises a portable signal transfer unit 12 having a receiver 12a in communication with a processor 12b which, in turn, enables two-way transfer of data and commands to base station 14 via a radio module 12c. Further details of a preferred form of unit 12 are given in a co-pending patent application entitled "Portable Signal Transfer Unit", U.S. patent application Ser. No. 09/292,158, which is incorporated herein by reference.

Base station unit 14 comprises a radio module 14a for receiving data signals from signal transfer unit 12, a processor 14b suitably programmed to manipulate the physiological data and to enable transfer from base station 14 to remote monitoring station 16 via a modem 14c and a link T. Remote monitoring station 16 can comprise a modem 16a and programmable computer 16b, for example. Further details of the base station 14 and remote monitoring station 16, as well as the system as a whole, including details of the format of transmitted data and transmission protocols between the device 10 and signal transfer unit 12, are given in a co-pending application entitled "Portable Remote Patient Telemonitoring System", U.S. patent application Ser. No. 09/292,405, which is incorporated herein by reference.

Figure 3:
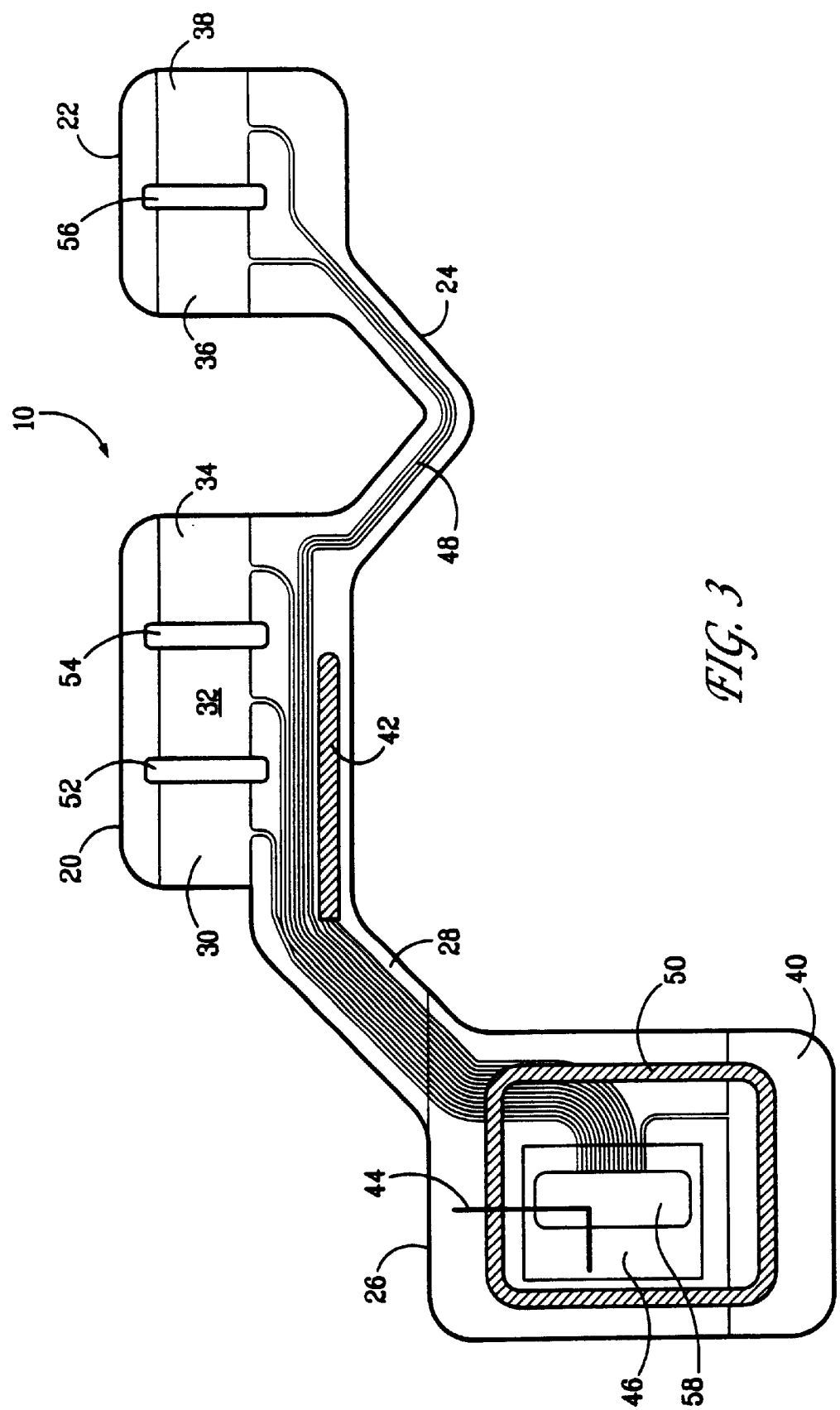
FIG. 3 is a schematic front elevation view of a device according to the invention.

FIG. 3 illustrates a front elevation view of a preferred embodiment of physiological sensor device 10 according to the invention showing the face of the device which is attached to a subject in use. Device 10 comprises a first sensor region 20, for positioning in a precordial position, and a second sensor region 22, connected thereto by a yoke or web 24. Device 10 further comprises a third sensor region 26, for positioning just below the subject's axilla under the subject's left arm. Third region 26 is attached to first region 20 by a web 28. First region 20 comprises three electrode sensors 30, 32 and 34, while second region 22 comprises two electrode sensors 36 and 38. A sixth electrode sensor is provided at the bottom of third sensor region 26 in the form of electrode 40. The electrode sensors can be used to monitor such physiological parameters as heart rate, respiration and/or motion as described below, and are operably in electrical contact with a patient's skin through the use of a conductive gel.

A further physiological sensor 42 is provided on first sensor region 20 proximal the web 28 and hence adjacent or at least proximal a subject's chest in use. Sensor 42 can be used to determine the extent of movement of a subject's chest and hence to monitor respiration, for example. The sensor 42 can comprise a bend sensor having a flexible nonconductive substrate onto which is mounted a strip of conductive material such as ink which in turn has a series of highly conductive areas, for example of metal, mounted on top of the conductive strip. The resistance of the conductive material varies according to the extent of bending of the flexible substrate. Such sensors are available from Abrams/Gentille Entertainment Inc of New York, N.Y., for example. The bend sensor 42 can be positioned anywhere on the chest but preferably is located between a precordial position and the axilla—such as over or adjacent the pectoral muscle. A further physiological sensor is provided in the form of a temperature sensor 44 which can for example comprise a thermistor.

A printed circuit board 46 is provided for the on-board electrical system having suitable electronics such as the ASIC 59 and micro-controllers 61 that are operably in communication with the various sensors via conductive traces 48. The system is able to communicate to a signal transfer unit 12 via an aerial or coil antenna 50 which beneficially can be substantially flat and rectangular to fit comfortably around PCB 46. Also shown in FIG. 3 is a series of slots 52, 54 and 56 which pass through sensor regions 20 and 22. These slots provide an air gap separation, and hence non-conductive divide, between adjacent electrodes and also provide additional flexibility to sensor regions 20 and 22. Also shown schematically in FIG. 3 is an aperture 58 which passes through the layers of device 10 to accommodate suitable batteries attached to printed circuit board 46.

In use, device 10 is attached to a patient such that first sensor region 20 is positioned in a precordial position on the chest, web 24 lies across the sternum and second sensor region 22 is located in substantial horizontal alignment with region 20, on the right hand side of the chest. Web 28 passes over the pectoral muscle of a subject, and third region 26 is preferably located just below the left axilla or left armpit of the patient.

Figure 4:
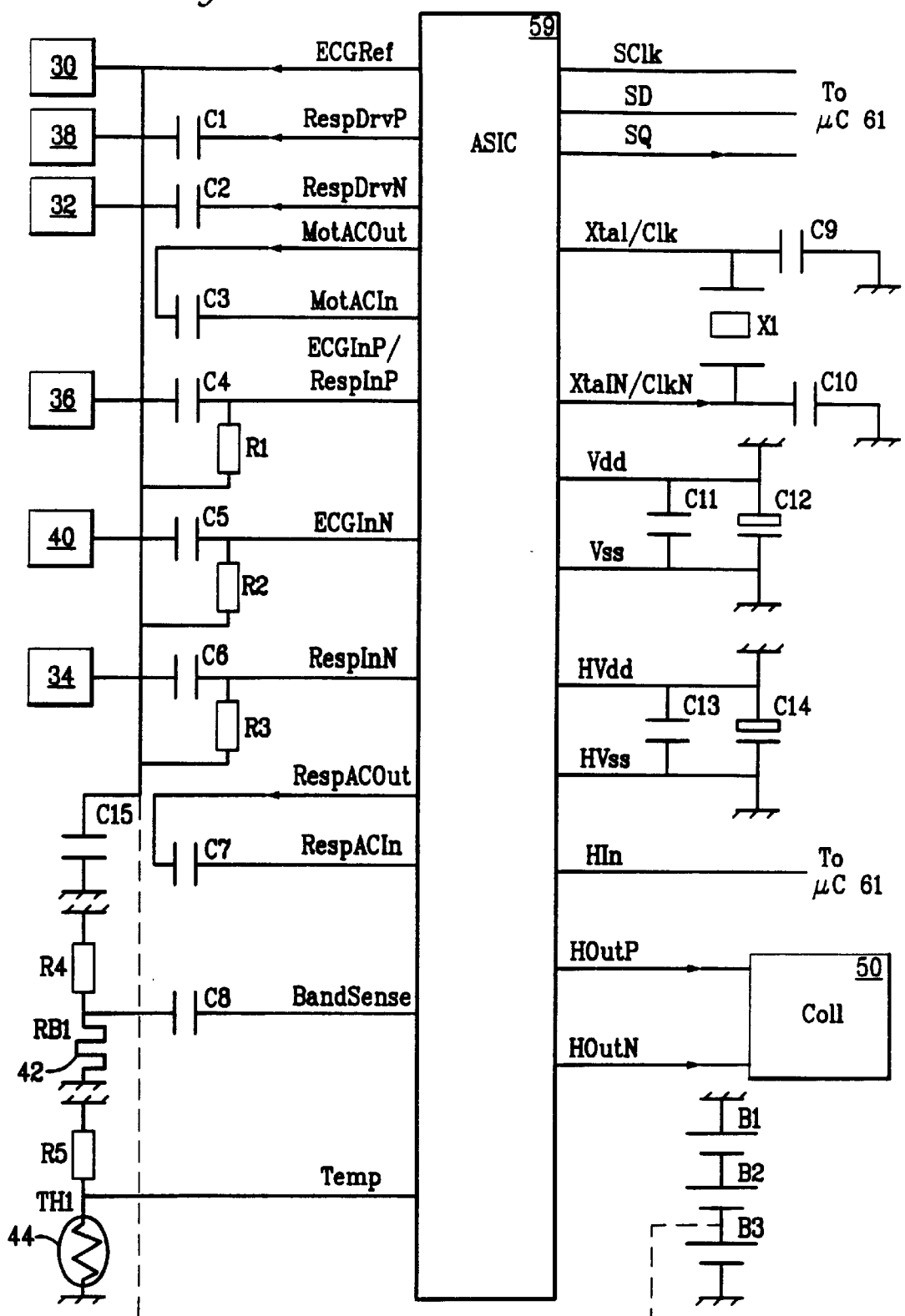
FIG. 4 is a schematic diagram of the connections of various sensors and other external devices to the ASIC of the invention.

The connection of the various sensors to ASIC 59 mounted on printed circuit board 46 is shown in FIG. 4. In a preferred embodiment, electrode 30 acts as an ECG reference electrode and electrodes 40 and 36 act as positive and negative sense ECG electrodes, respectively. Preferably, the three electrode sensors act to approximate the standard BCG lead II signal. Of course, other combinations of electrodes 30, 32, 34, 36, 38 and 40 could be used as the reference, positive and negative sense ECG electrodes where preferably the reference electrode is as far away as possible from the positive and negative sense electrodes as possible. The present arrangement is particularly adapted for common use of one of the electrodes as part of the respiration sensor as well as the ECG sensor.

Electrode 36 also acts as a respiration sensor as do electrode sensors 32, 34 and 38, which utilization is described in greater detail below. Additionally, bend sensor 42 is connected to ASIC 59 through a voltage divider and filter configuration comprising resistor R4 and capacitor C8. Temperature sensor 44 comprises a thermistor TH1 connected to ASIC 59 through a voltage divider arrangement comprising resistor R5.

Power to the electronic system is provided by a battery which in this embodiment comprises three 1.4 volt zinc-air cells B1–B3 such as DA675 cells, which in series provide a maximum of approximately 4.2 volts between power rails on PCB 46. In fact the majority of components require a 2.5 volt source and the use of three 1.4 volt cells has been found to provide a suitable power source for the required operational duration of about 24 hours for the system.

Figure 5:
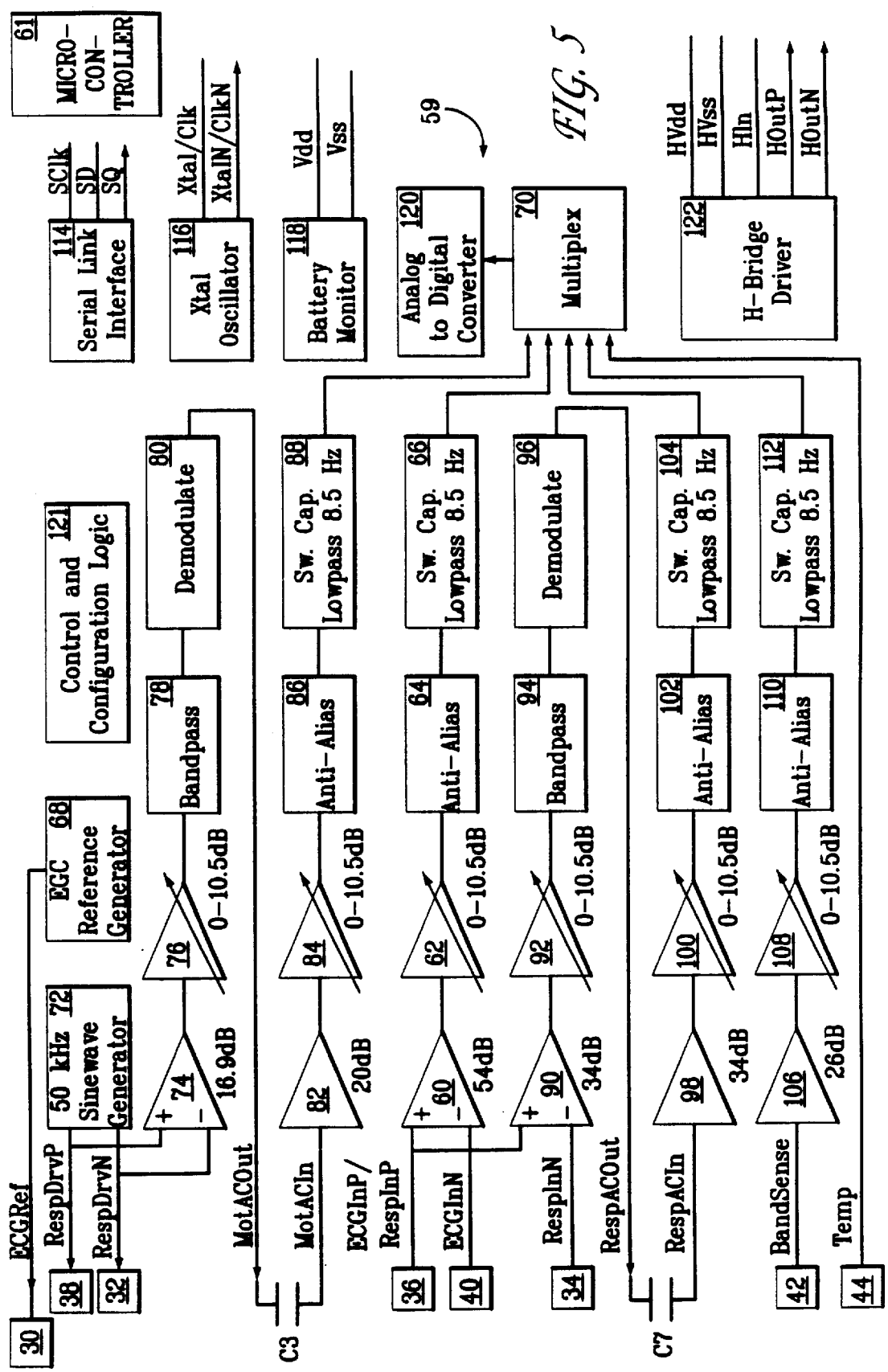
FIG. 5 is a schematic block diagram of the electronic system forming the device or array of the invention.

Further description of the various pins identified in FIG. 4 is given in Table 1, and a further block diagram of the functional components of ASIC 59 and external components is provided in FIG. 5.

The ECG sensor or circuit, illustrated in FIGS. 4 and 5, is required to amplify a small differential voltage from two chest electrodes 36, 40 (sensed on the ECGInP/RespInP and BCGInN Pins of ASIC 59), while rejecting a much larger common mode signal. A third electrode 30 connected to the ECGRef pin acts as a ground reference. The signals are AC coupled into the ASIC 59 using an off-chip RC network (FIG. 4). The ASIC 59 amplifies and filters the input signal, and has provision for adjustable gain and offset The filtered ECG signal is preferably sampled at 250 Hz and converted to a digital signal by the A/D converter 120.

In greater detail the ECG circuit comprises a differential or operational amplifier 60 connected to electrode sensors 36 and 40 as shown in FIG. 5. Amplifier 60 can for example provide 54 dB amplification. The signal is then fed to a variable amplifier 62 of between 0 to 10.5 dB. The ECG signal passes through an anti-aliasing device 64 to facilitate proper sampling in the following switched capacitor filter. The output signal then passes to a switched capacitor low pass circuit 66 which in turn is fed to multiplexer 70.

A high frequency cut off of 85 Hz might be provided by switched capacitor low pass circuit 66, but this can be altered, for example, by changing the crystal frequency of the crystal oscillator 116 thereby to increase the high frequency cut off from 85 Hz to 100 Hz, for example.

Temperature sensing is done using an off-chip thermistor/resistor potential divider. A single pin Temp on the ASIC 59 is used to interface to the temperature sensor 44. No signal conditioning need be performed, instead the voltage is multiplexed directly into the A/D converter 120. Preferably A/D converter 120 uses $V_{DD}$ as a reference voltage, hence variations due to changing battery voltage are canceled. Conversion of this digital value into a temperature value is done externally to the ASIC 59. Skin temperature data can be collected at 25 Hz. Preferably, the range of temperatures monitored by thermistor 44 is between 25 and 45° Centigrade with an accuracy of about +/–0.5° C.

One method of respiration measurement uses tetrapolar electrodes to detect changes in the impedance of the body's chest cavity. One pair of electrodes 38,32 is driven with a reciprocating current from the RespDrvP and RespDrvN pins, which causes a voltage to be developed across the body in proportion to its impedance. For example, a 50 kHz sine wave generator 72 can be used. Electrodes 34 and 36 are used to sense the voltages. One electrode 36 is shared with an ECG input (pin EcgInP/RespInP), and the other electrode 34 connects via pin RespInN to ASIC 59. These inputs are fed to a first stage amplifier 90 for example providing 34 dB amplification from which the signal is passed to a variable amplifier 92 enabling further amplification from between say 0 to 10.5 dB. The signal passes through a band pass filter 94 and on to demodulation circuitry 96. The demodulation circuitry 96 preferably consists of a precision rectifier followed by a low pass filter, which gives better performance than a peak detector type circuit in the presence of noise.

The demodulated respiration signal is capacitively coupled via capacitor C7 to pin RespACIn and passes through a second stage amplification comprising, for example, a 34 dB amplifier 98 and variable amplifier 100 (again between 0 and 10.5 dB preferably) and on to an anti-aliasing device 102. Finally, the signal passes through switched capacitor low pass filter circuit 104 before being passed onto multiplexer 70. The demodulator 96 and second gain stage and filter (98 to 104) can be independently powered down if not required (e.g. if the alternative method of respiration measurement is used). As can be seen, two pins RespACOut and RespACIn on ASIC 59 are used with an off-chip capacitor C7 to AC couple the demodulated respiration signal to the second gain stage.

Respiration can also be measured using bend sensor 42. This method uses a resistance bend sensor 42 for respiration measurement which sensor has an impedance which in a preferred embodiment typically varies between 12 k$\Omega$ when flat and 40 k$\Omega$ when bent through 90 degrees. The change in impedance when used as a respiratory monitor is generally about 500–1000 $\Omega$. In another example, a bend sensor having a variable impedance of between 26 k$\Omega$ and 200 k$\Omega$ (between 0° and 90° of bend) can provide a variation in impedance of between 500 $\Omega$ and 2000 $\Omega$ during normal respiration. Beneficially, deep breaths can be detected using such bend sensors by a large variation in impedance of around 5 k$\Omega$. Bend sensor 42 can comprise a sensor having a flexible non-conductive substrate onto which is mounted a strip of conductive material such as ink which in turn has a series of highly conductive areas for example of metal mounted on top of the conductive strip. Such sensors are available from Abrams/Gentille Entertainment Inc of New York, for example. In one embodiment, the conductive track is U-shaped having an electrical contact at the end of each of the arms of the track.

The bend sensor 42 is connected in series with an external resistor R4. This combination is connected across the supply rails, thus acting as a potential divider. The midpoint of the divider is AC coupled into the ASIC 59 via the BendSense pin. The signal is then amplified via amplifiers 106 (e.g., 26 dB) and 108 (e.g. 0–10.5 dB), passed through anti-aliasing device 110 and filtered at switched capacitor filter 112 before being driven into the multiplexer 70.

An impedance measurement for motion detection is preferably also obtained from the monitored voltage between the respiration (impedance) drive electrodes 38 and 32, i.e., at the RespDrvP and RespDrvN pins. The demodulator and gain/filter stage are similar in principle to that of the Respiration (Impedance) channel, and can be independently disabled. As shown in FIG. 5, it can be seen that a differential amplifier 74, of say 16.9 dB, is connected to the outputs from sine wave generator 72 to electrodes 38 and 32. The differential output signal is passed through a variable amplifier 76 (of say between 0 and 10.5 dB) and subsequently through band pass filter 78 and demodulation circuitry 80. The output from the demodulation circuitry 80 is AC coupled via capacitor C3 to amplifier 82 (of say 20 dB) and then on to variable amplifier 84 (of say 0 to 10.5 dB).

The signal then passes through anti-aliasing circuitry 86 and a switched capacitor low pass filter circuit 88. The output signal is finally fed to multiplexer 70.

The movement detection is accordingly an effective measurement of variations in the impedance between electrode sensors 32 and 38. This impedance variation is most likely to be caused due to variations in the electrical conductance of the conductive gel between the electrode and the user's skin, whereby movement of the subject causes some movement of device 10 and hence minor variations at the conductive interface between device 10 and the patient can be detected. The size of signal detected can be used to determine the extent of movement. Alternatively, a threshold value for the detected movement signal can be predetermined such that signals below the threshold value indicate that the patient is substantially stationary whereas signals above the threshold value indicate that the patient is undergoing some form of movement.

Accordingly, in the illustrated embodiment, five different sets of physiological data are gathered by the various sensors and suitably demodulated, filtered and passed through to multiplexer 70. In turn, multiplexer 70 sequentially feeds the appropriately sampled signals in a predetermined sequence through to analog to digital converter 120. Also, ASIC 59 comprises a control and configuration logic unit 121 to provide control and proper timing of certain operations within the ASIC 59.

The analog signals from the various sensor channels are converted into digital values using an on-chip Analog to Digital (A/D) converter 120, where the input of the A/D converter is multiplexed between the various sensor channels. The A/D converter 120 may use an on-chip resistor chain connected across the power supply as a reference. Beneficially, the A/D converter 120 can be powered down when inactive (i.e., between samples) and can be a successive approximation type converter with 10 bit resolution, for example.

The ASIC 59 also has two pins (Xtal/Clk and XtaIN/ClkN) dedicated to a crystal oscillator circuit 116. If the on-chip crystal oscillator is used, then an external crystal and two capacitors should be connected. A clock signal can then be taken from the XtaIN/ClkN pin. If an external clock signal is used then the external crystal and capacitors should preferably be removed and the external clock driven into the Xtal/Clk input.

Commands and data are passed between the ASIC 59 and one of the external micro-controller devices 61 via a 3-wire link (pins SD, SQ, SClk) serial link interface 114. This micro-controller can write into various configuration registers within the ASIC 59, and can read data from any of the sensor channels using the Analog to Digital converter 120 on the ASIC 59. The serial port forming interface 114 consists of three wires:

1. SClk (serial clock): This is an input to the ASIC 59.
2. SQ (serial data output): This output carries the measurement data and other information from ASIC 59 to one of the micro-controllers 61.
3. SD (serial data input): This input will carry the commands and data into the ASIC 59 from micro-controller 61.

The serial link interface 114 supports three types of operation: commands, read operations, and write operations. Commands are performed by clocking an eight bit operation code into the ASIC 59. For register write operations, a further byte of data is clocked into the ASIC 59. For register read operations, up to ten bits of data are clocked out on the SQ pin after the operation code has been received.

The rising edge of SClk is active, and data on the SD pin is read on the rising edge. Data changes on the SQ pin happen subsequent to a rising edge. The signal SClk need not in be clocked continuously. The ASIC 59 recognizes the beginning of an operation code when a logic 1 is clocked in. When SClk is toggling but an operation code is not being clocked into the ASIC 59 (e.g., when read data is being clocked out), then SD should be held at logic 0.

Figure 6:
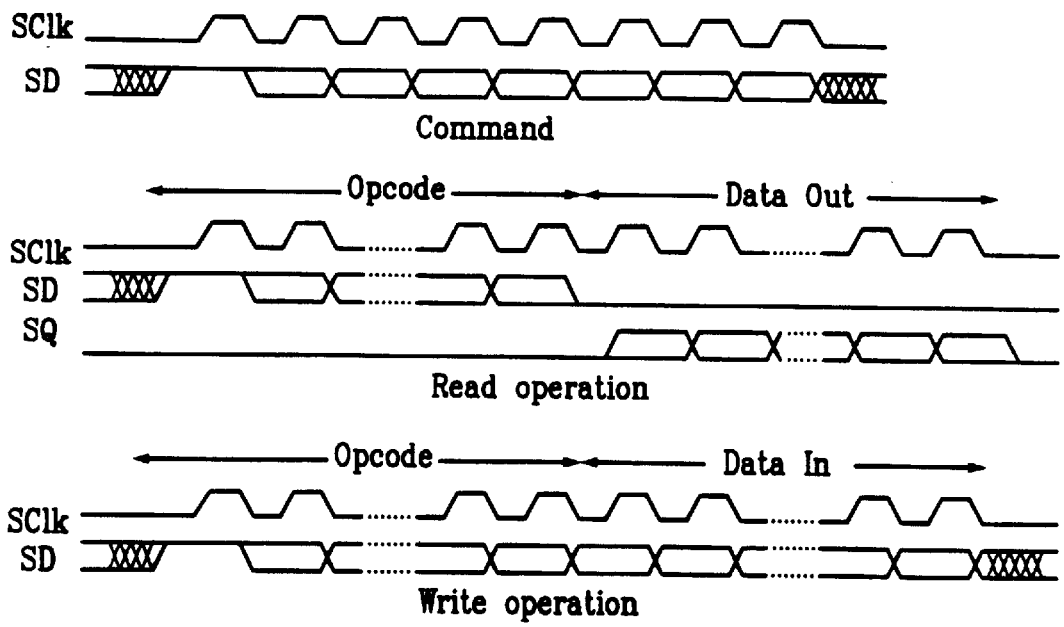
FIG. 6 is a pulse diagram of the timing sequences for communication between the ASIC and one of the micro-controllers via a serial link.

An example of Command, Read, and Write operations is shown in FIG. 6.

The ASIC 59 has a collection of registers which may be read or written to via serial port 114. These hold various data such as the values on the sensor channels, configuration settings, and status information. Write commands are followed by eight bits of data, with the most significant bit being clocked in first. For read commands, the SQ pin goes to the value of the MSB of the output word on the first clock edge after the operation code has been received. Each active clock edge clocks the next least significant bit out of the ASIC 59. After the LSB has been output, SQ goes to logic 0 and remains in that state until another register read operation code is received by the ASIC 59.

Figure 7:
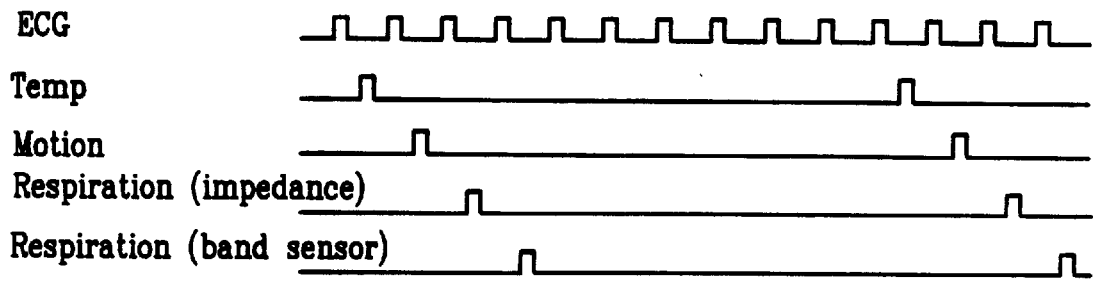
FIG. 7 is a pulse diagram showing the preferred 250 Hz ECG sample frequency, and 25 Hz sample frequency for other physiological parameters over a 40 millisecond time frame.

The crystal oscillator 116 (on chip or from an external source) is divided down to provide the clock for the switched capacitor filters and the A/D converter 120. The outputs of the switched capacitor and after (SC) filters (66, 88, 104, 112) naturally have periods between clock pulses where their outputs are stable, which would be the most desirable place for the A/D converter 120 to do a conversion. However, because the external micro-controllers 61 cannot be guaranteed to be running in exact lock-step with the ASIC 59, there is a danger that samples could be dropped occasionally. Therefore the ASIC 59 preferably only does a conversion on one of the sensor channels when explicitly instructed to do so by one of the micro-controllers 61 (via the serial link 114). Requests for ECG conversions are issued by one of the micro-controllers 61 at, in this example, a precise 250 Hz rate, with requests for motion, respiration and temperature measurements being interleaved between the BCG measurements at a 25 Hz rate, as shown in FIG. 7. FIG. 7 shows the position of measurements in a 40 ms repeating time frame.

Since the SC filter clocks and the micro-controller clock are not necessarily synchronized, it may be that the A/D converter 120 will be instructed to do a conversion while the filter outputs are in transition between two adjacent samples. However, as the A/D converter 120 gives an output that is somewhere between the two adjacent levels, there are no large spikes or spurious values. Also, clock noise does not cause a problem since the SC filters have smoothing filters on their outputs to remove this. However, the A/D converter 120 can be configured (using a register bit) to delay its conversion until the SC filter outputs have settled.

If the power supply voltage drops below a certain threshold, the SC filters will no longer operate correctly. In order that one of the external micro-controllers 61 can determine the integrity of the sensor measurements, a battery monitor circuit 118 (FIG. 5) periodically measures whether the supply voltage is adequate, and updates a bit in the status register accordingly.

The ASIC 59 preferably has a built in power-up reset function which puts the device into a defined state when power is first applied. It then waits for a predetermined time for the power supply and clock to settle. The power-up delay function preferably comprises a length of power-up sequence of 100 ms maximum (after power supply settles), and a power supply settling time of 100 ms maximum to within 5% of the final value. The power supply voltage preferably increases monotonically. Power-up can occur on removing an air impermeable membrane from the batteries B1, B2 and B3.

A wireless communication link is used to communicate between the sensor array, that is device 10, and the signal transfer unit 12. As a backup option, the same drive circuit can be used to drive via a wire link (not shown). The ASIC 59 can contain an H-bridge driver 122 for this purpose. One of the external micro-controllers 61 drives data for the H-bridge onto the Hin pin, the external antenna 50 being connected to the HOutP and HOutN pins. The ASIC 59 has protection circuitry to prevent the coil driver from drawing excessive current from the battery at power up the H-bridge driver is reset to an inactive state, and during normal operation the H-bridge driver will be deactivated if there have been no data transitions for a certain amount of time.

The driver 122 comprises transistors which carry high peak currents, and can carry bi-directional current to allow energy to be recirculated into the supply. In order to minimize coupling or interference in the sensor amplifier circuits, the H-bridge driver preferably has its own dedicated power supply pins $HV_{DD}$ and $HV_{SS}$. These pins preferably have good external decoupling.

In a preferred embodiment, the H-bridge driver specification is as follows:

| | |
|---|---|
| Output resistance | 1 Ω max. |
| Output capacitance (per pin) | 500 pF max. |
| Drive transistor turn on time | 100 ns max. |
| Timeout delay | 32 µs. |

The purpose of the coil-driving circuitry 122 in the transmitter is to deliver sufficient signal current into the primary coil to yield the required magnetic field strength at the receiving coil (on signal transfer unit 12) while incurring minimal energy loss, and thus minimizing supply current.

In order to save power in its circuitry, it is necessary to avoid resistive losses in the output stages of the transmitter. This may be achieved by avoiding the use of a linear output stage and instead using switching circuitry. Switching devices may be used to apply the power supply directly to the transmitter coil 50 and will in principle result in no power loss, since perfect switches dissipate no power in either their on or off states. Practical switches may be implemented using transistors, such as those present in the output stages of digital integrated circuits. A switching output stage is more easily applicable to drive signals having a constant amplitude, such as frequency or phase modulation, including direct spread-spectrum digital modulation. Amplitude modulation may be achieved, but at the expense of the complication of pulse-width modulation, where the duty cycle of the output may be varied.

Two ways are available to recycle the energy used in building up the magnetic field during each voltage cycle applied to the coil. In the case of a narrow-band transmission system, the coil 50 may be resonated at the transmitted frequency using a capacitor connected across it. Each time the magnetic field in the coil 50 collapses, the energy released passes into the capacitor, where it is stored as charge. When the field has completely collapsed, the energy now stored in the capacitor starts to return to the coil 50 to build up the field in the opposite direction to give, in principle, a lossless system. In practice, of course, there will be residual losses from the series resistance of the coil 50, so a drive circuit is necessary. Either a voltage drive may be used to drive a series resonant circuit, or a current drive may be used with a parallel resonant circuit. At typical circuit impedance levels, the power supply in electronic equipment is usually better considered as a voltage source, so a switching circuit driving a voltage square wave into a series resonant circuit will be appropriate.

Apart from the limited frequency band over which it is effective, a drawback of using resonance is that the impedance level of the coil 50 is altered. In the case of a series resonant circuit for example, the impedance of the circuit at resonance is simply that of the self resistance of the coil, which will intentionally be low to reduce losses. For a given power supply voltage, this may result in an inappropriately high current in the coil. A coil resistance of 5 Ω, for example, would lead to a current of 1A when fed from a 5V supply.

Figure 8:
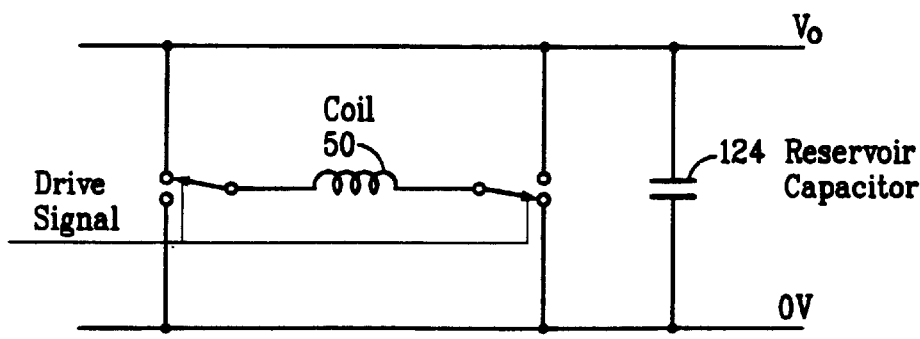
FIG. 8 is a schematic diagram of the drive arrangement to the transmission coil.

An alternative technique, which overcomes the drawbacks of the resonant circuit is to drive the coil 50 using switches in a bridge configuration as shown in FIG. 8. In this configuration, the energy from the collapsing magnetic field is returned to the power supply, ready for the next cycle. For this technique to succeed, the power supply must be able to store the returned energy, which is easily arranged by the use of a reservoir capacitor 124. The resulting circuit may be used at any frequency (in principle), while the self-inductance of the coil 50 acts as a convenient way of defining the output current. The switches may be electronic devices, such as discrete transistors or components in the output stages of ASIC 59.

Figure 9:
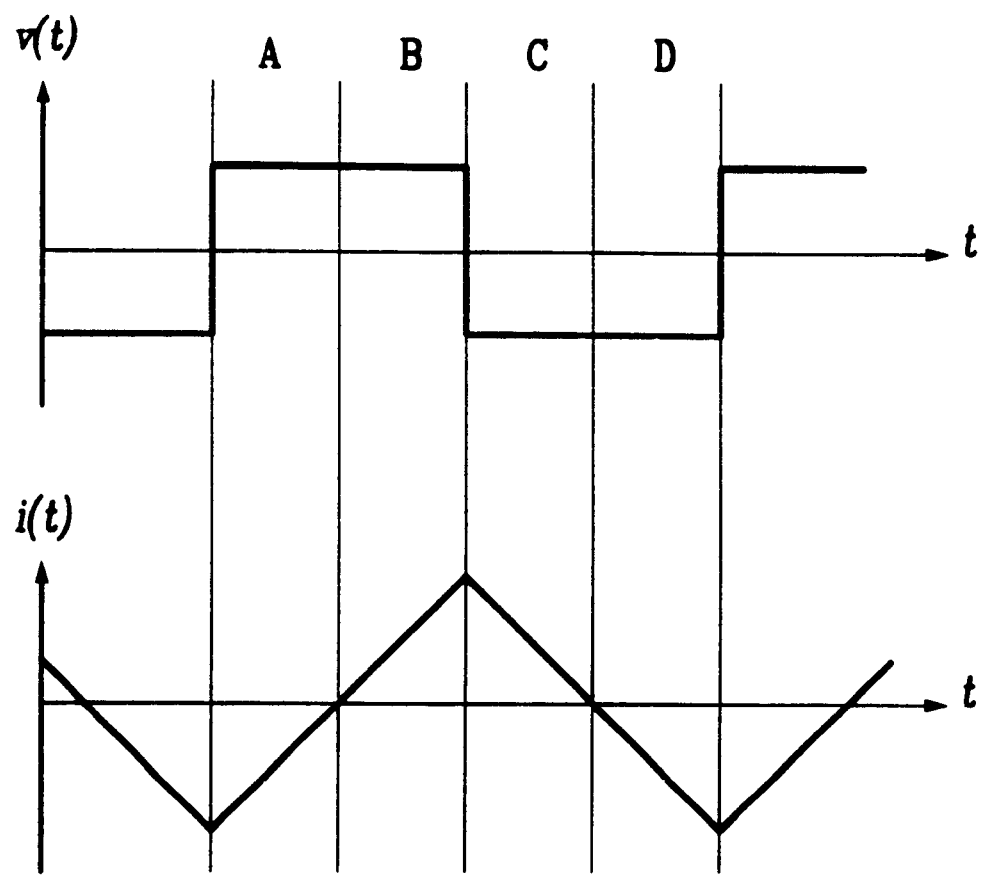
FIG. 9 is a schematic waveform diagram for the operation of the drive circuit shown in FIG. 8.

The operation of this circuit is illustrated by the waveforms given in FIG. 9, which show the voltage v(t) applied to the coil and the resulting current i(t) for the case of a continuous square wave drive signal and a perfect circuit exhibiting no resistive losses. During intervals A and B, the applied voltage is positive, so the current linearly increases, while for intervals C and D, the applied voltage is negative, so the current linearly decreases. During intervals B and D, the current has the same polarity as the applied voltage, indicating the energy is being supplied to the coil and a magnetic field is being built up. During intervals A and C, the current has the opposite polarity to the applied voltage, indicating that energy is being transferred from the coil 50 to the supply as the magnetic field collapses.

In the bridge-drive circuit described above, to the coil 50 is always applied a voltage of the same magnitude as the supply voltage, but of alternating polarity. The circuit is thus only suitable for two-valued drive signals, though these may form a pulse-modulated signal representing a lower frequency waveform. By separating the drive signals to two push-pull bridge output stages, the coil 50 may be fed with a third drive level of zero voltage. In this state, the magnetic field in the coil 50 is maintained, ideally without loss. The result is that a third signal value may be used, which may allow a better representation of signals by pulse modulation.

The circuit may be further extended by the use of additional supply lines at different voltage levels, each fitted with energy storage capacitors and connected to both ends of the primary coil 50 by means of switching devices. Care must be taken in the selection of switching signals to ensure that the energy into and out of each capacitor is balanced over the long term. Using this arrangement the digital multiplexed signals from ADC 120 are transmitted on a pre-selected carrier frequency via inductive coupling of coil 50 to a remote receiver coil in a signal transfer unit 12.

In this regard a variety of protocols for the modulation of a fundamental carrier frequency such as between say 50 kHz and 150 kHz and preferably between 54 kHz and 144 kHz is described in our co-pending patent application entitled "Portable Remote Patient Telemonitoring System", U.S. patent application Ser. No. 09/292,405 As described therein, in a preferred embodiment, a quadrature phase shift keying (QPSK) technique is used whereby the binary data is transmitted in bit pairs and each consecutive bit pair corresponds to a different phase offset of 0, 90, 180 or 270° of the transmitted signal relative to the fixed carrier. In a preferred embodiment, digital modulation in a 4 kHz band on channels with 6 kHz separation in the above frequency range is preferred.

Preferably, a randomly generated unique serial number is generated for each device 10 and inserted in the data for transmission and hence easy tracking of the individual device 10. Of course, ordered serial numbers can be used for each of devices 10 manufactured but in the preferred form a random number generator such as a pre-programmed microchip is used to assign the serial number which is stored on one of the micro-controllers 61. In a preferred embodiment, one of the micro-controllers 61 comprises its own random number generator. Accordingly, a randomly generated number is selected by one of the micro-controllers 61 to represent the serial number for a given device 10.

Although an exemplary embodiment of the invention has been described in detail above, those skilled in the art will readily appreciate that many additional modifications are possible in the exemplary embodiment without materially departing from the novel teachings and advantages of the invention. All such modifications are intended to be included within the scope of this invention as defined in the following claims.

TABLE 1

| Pin Name | Direction | Description |
| --- | --- | --- |
| $V_{DD}$ | I/O | Power connection |
| $V_{SS}$ | I/O | Ground connection |
| Xtal/Clk | Input | Crystal/Clock input |
| XtalN/ClkN | Output | Crystal/Clock output |
| SD | Input | Serial link data input |
| SQ | Output | Serial link data output |
| SClk | Input | Serial link clock |
| ECGRef | Output | ECG reference connection |
| ECGInP/ | Input | ECG sense (+) |
| RespInP | | Respiration (impedance) sense (+) |
| ECGInN | Input | ECG sense (−) |
| Temp | Input | Temperature sensor input |
| RespDrvP | Output | Respiration (impedance) current drive (+)/ Motion sense (+) |
| RespDrvN | Output | Respiration (impedance) current drive (−)/ Motion sense (−) |
| RespInN | Input | Respiration (impedance) sense (−) |
| RespACOut | Output | Respiration AC coupling output |
| RespACIn | Input | Respiration AC coupling input |
| BendSense | Input | Respiration (bend sensor) input |
| MotACOut | Output | Motion AC coupling output |
| MotACIn | Input | Motion AC coupling input |
| $HV_{DD}$ | I/O | H-Bridge Power connection |
| $HV_{SS}$ | I/O | H-Bridge Ground connection |
| HIn | Input | H-Bridge input signal |
| HOutP | Output | H-Bridge output drive (+) |
| HOutN | Output | H-Bridge output drive (−) |

What we claim is:

1. A physiological sensor device for attachment to a mammalian subject comprising an output transmitter, at least two physiological sensors each for sensing one of the subject's physiological parameters, and a controller operably in communication with the physiological sensors which controller samples outputs of said sensors at different sampling rates and communicates a signal comprising data representative of both the sensed physiological parameters to said output transmitter, which operably transmits the signal to a remote location, wherein the controller comprises a multiplexer which interleaves the sampled data from the physiological sensors into a serial output signal.

2. A physiological sensor device according to claim 1 wherein the multiplexer is implemented in an application specific integrated circuit (ASIC).

3. A physiological sensor device according to claim 2 wherein the output transmitter enables wireless transmission of the signal to the remote location.

4. A physiological sensor device according to claim 1 wherein the controller samples an analog signal from the physiological sensors and converts the sampled analog signal into a digital signal for presentation to the output transmitter.

5. A physiological sensor device according to claim 1 wherein said at least two physiological sensors comprises at least two from an ECG sensor, a respiration sensor, a motion sensor, and a temperature sensor.

6. A physiological sensor device according to claim 5 wherein said at least two physiological sensors comprises a first respiration sensor and a second respiration sensor.

7. A physiological sensor device according to claim 6 wherein at least one of the first respiration sensor and second respiration sensor comprises a bend sensor.

8. A physiological sensor device according to claim 1 wherein a first physiological sensor operably detects ECG data and the controller operably communicates a signal representative of the ECG data to the output transmitter at a first sampling frequency, and a second physiological sensor operably detects at least one of respiration, motion, and temperature data and operably communicates a signal representative of said at least one data at a second sampling frequency to the output transmitter.

9. A physiological sensor device according to claim 8 wherein the first sampling frequency is greater than the second sampling frequency.

10. A physiological sensor device according to claim 9 wherein the first sampling frequency is approximately ten times greater than the second sampling frequency.

11. A physiological sensor device according to claim 10 wherein the first sampling frequency is on the order of 250 Hz.

12. A portable physiological sensor device comprising a plurality of electrode sensors for use in measuring electrocardiographic data and respiratory data of a subject, wherein at least one of the electrode sensors is used in both the electrocardiographic and respiratory measurements, wherein a signal from at least one of said plurality of electrode sensors is sampled periodically at a first sampling frequency by an ECG measuring device and periodically at a second sampling frequency by a respiration measuring device, and an output transmitter responsive to outputs of said electrode sensors so as to enable wireless transmission of the electrocardiographic data and respiratory data to a remote location.

13. A physiological sensor device according to claim 12 wherein the first sampling frequency is greater than the second sampling frequency.

14. A physiological sensor device according to claim 13 wherein the first sampling frequency is approximately ten times greater than the second sampling frequency.

15. A physiological sensor device according to claim 14 wherein the first sampling frequency is on the order of 250 Hz and the second sampling frequency is on the order of 25 Hz.

16. A physiological sensor device for attachment to a mammalian subject comprising a sensor for acquiring physiological data about the subject in use, and an output transmitter which receives a signal representative of the physiological data from the sensor and transmits the signal to a remote location, wherein the output transmitter comprises an inductive element for inductively coupling the output transmitter to a remote receiver at the remote location.

17. A physiological sensor device according to claim 16 wherein the output transmitter comprises a reservoir capacitor in parallel with the inductive element.

18. A physiological sensor device according to claim 16 wherein the inductive element has first and second ends each of which ends is connected via a pair of switches to signal supply lines within the output transmitter to enable a reversing of the polarity across the inductive element between the supply lines.

19. A physiological sensor device according to claim 16 wherein the inductive element comprises a coil which forms part of an H-bridge circuit in the output transmitter.

20. A physiological sensor device according to claim 16 wherein the inductive element comprises a rectangular substantially flat coil.

21. A physiological sensor device for attachment to a mammalian subject, having one or more physiological sensors, an output transmitter for transmitting a signal from the one or more physiological sensors to a remote location, a memory for storing a serial number for identifying the physiological sensor device which serial number is transmittable by the output transmitter with the signal, and a random number generator and a controller for selecting a randomly generated number from the random number generator and storing the selected randomly generated number as the device serial number in the memory.

* * * * *